(12) United States Patent
Phanstiel, IV et al.

(10) Patent No.: US 8,497,398 B1
(45) Date of Patent: Jul. 30, 2013

(54) POLYAMINE TRANSPORTER SELECTIVE COMPOUNDS AS ANTI-CANCER AGENTS

(75) Inventors: Otto Phanstiel, IV, Oviedo, FL (US); Navneet Kaur, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 631 days.

(21) Appl. No.: 12/113,540

(22) Filed: May 1, 2008

Related U.S. Application Data

(60) Provisional application No. 60/915,448, filed on May 2, 2007.

(51) Int. Cl.
  *C07C 211/00* (2006.01)
  *C09B 11/02* (2006.01)
  *A61K 38/00* (2006.01)
  *A61K 47/00* (2006.01)

(52) U.S. Cl.
  USPC ............. 564/305; 564/308; 564/315; 514/1.2

(58) Field of Classification Search
  None
  See application file for complete search history.

(56) References Cited

U.S. PATENT DOCUMENTS 7,208,528 B1 * 4/2007 Vermeulin et al. ............ 514/626

OTHER PUBLICATIONS

Gardner et al. J. Med. Chem. 2004, 47, 6055-6069.*
Kaur et al. J. Med Chem. 2008, 51, 1393-1401.*

* cited by examiner

*Primary Examiner* — Sudhakar Katakam
*Assistant Examiner* — Clinton Brooks
(74) *Attorney, Agent, or Firm* — Timothy H. Van Dyke; Beusse, Wolter, Sanks, Mora & Maire, P.A.

(57) ABSTRACT

Several aromatic hydrocarbons di-substituted with a polyamine are described according to formulas selected from compounds 4, 7, 10, 15 and pharmaceutically acceptable salts thereof. The novel dimeric polyamines of the present invention demonstrate enhanced penetration into cells having an upregulated polyamine transport system, such as various types of cancer cells. The disclosed aromatic polyamine dimers provide highly efficient drugs for targeting cancer cells with active polyamine transporters.

3 Claims, 6 Drawing Sheets

US 8,497,398 B1

POLYAMINE TRANSPORTER SELECTIVE COMPOUNDS AS ANTI-CANCER AGENTS

RELATED APPLICATION

This application claims priority from provisional application Ser. No. 60/915,448, which was filed on May 2, 2007, and which is incorporated herein by reference in its entirety.

FIELD OF THE INVENTION

The present invention relates to the field of cancer treatment and, more particularly, to polyamines which, due to their special structure, preferentially enter cells having an upregulated polyamine transport system.

BACKGROUND OF THE INVENTION

Polyamines are essential growth factors for cells. All cells have methods of manufacturing polyamines from aminoacid sources. In addition cells can import polyamines from outside the cell via a process referred to as the polyamine transporter (PAT). While much is known about polyamine transport in bacteria, yeast and *Leishmania* spp., the mammalian polyamine transporter is a measureable, yet poorly described import process. It is an important cancer target because many cancer cells are unable to produce enough polyamines to sustain their growth rate and rely on polyamine import in order to grow. Accordingly, certain polyamines are important vectors for delivery of agents into cells via the cells' polyamine transport system.

SUMMARY OF THE INVENTION

With the foregoing in mind, the present invention advantageously provides several aromatic hydrocarbons di-substituted with a polyamine. These compounds are useful treatment agents and gain entrance into cells via the cell's own polyamine transport system. In this manner, one can append a polyamine architecture to a polycyclic aromatic architecture and facilitate its import into cells via the polyamine transporter. In this sense, the polyamine acts as a drug delivery 'vector', which assists cellular uptake of the attached aromatic system. The presently disclosed hydrocarbons have formulas according to compounds 4, 7, 10, 15, as shown in the figures, and include pharmaceutically acceptable salts thereof as well as conjugates.

The invention also includes a pharmaceutically acceptable composition containing at least one aromatic hydrocarbon di-substituted with a polyamine, said hydrocarbon's formula being selected from compounds 4, 7, 10, 15 and pharmaceutically acceptable salts thereof.

The invention further includes a method of treating a cell, the method comprising contacting the cell with a compound or conjugate selected from compounds 4, 7, 10, 15, combinations thereof and their pharmaceutically acceptable salts. Preferably, in the method the cell being treated is a cancer cell or a cell with an increased level of topoisomerase IIa. Where the cell being treated expresses an increased level of topoisomerase IIa and the compound, conjugate, combination or pharmaceutically acceptable salt selected preferably comprises compound 4.

The invention additionally includes several conjugates employing compounds 4, 7, 10 and 15 as treatment agents which are delivered via a cell's own polyamine transport system. For example, the invention includes an anthracene conjugate di-substituted with homospermidine, wherein said conjugate's formula comprises compound 4 or pharmaceutically acceptable salts thereof. Also included is a naphthyl conjugate di-substituted with homospermidine, wherein said conjugate's formula comprises compound 7 or pharmaceutically acceptable salts thereof. Part of the invention is a benzyl conjugate di-substituted with homospermidine, wherein said conjugate has a formula selected from compounds 10, 15, mixtures thereof and pharmaceutically acceptable salts thereof.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

Figure 1:
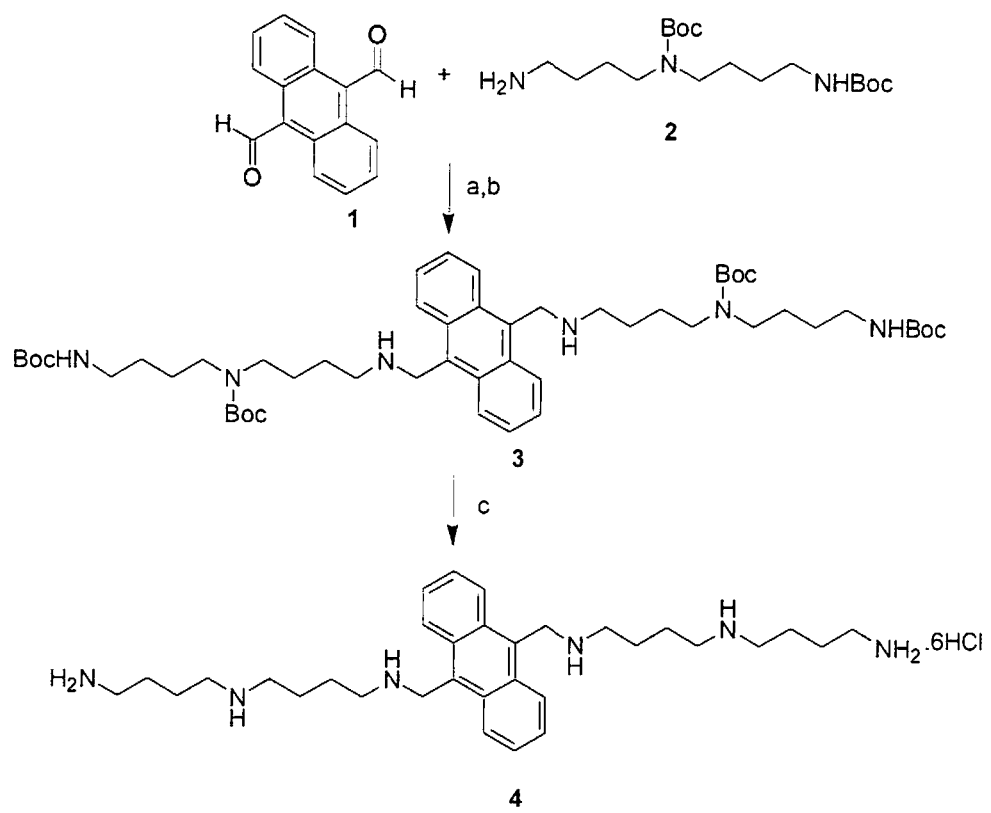
FIG. 1 is a chemical flow diagram showing a synthetic scheme for making compounds 3 and 4 according to an embodiment of the present invention.
Figure 2:
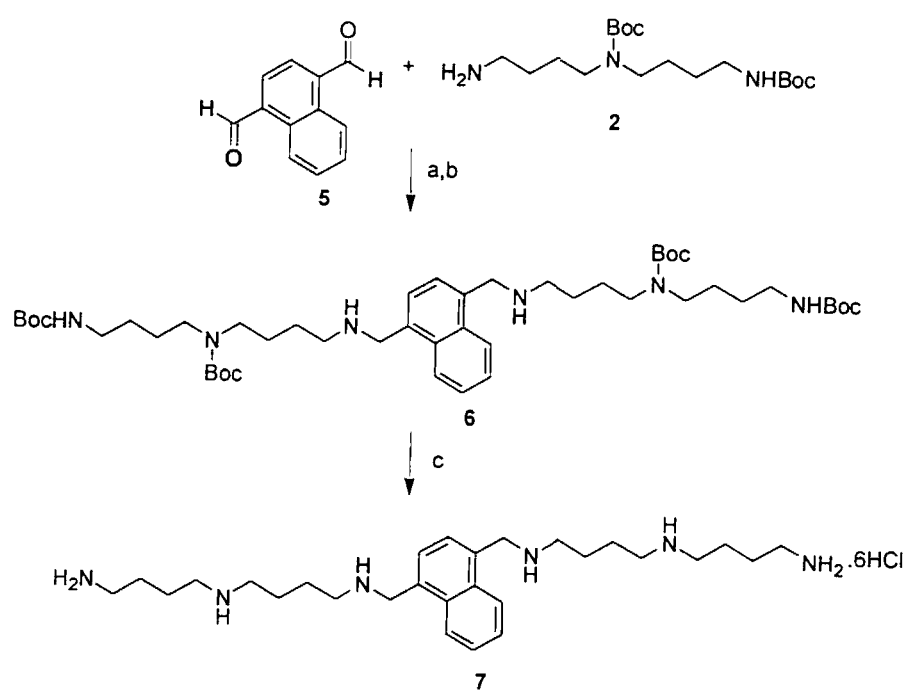
FIG. 2 shows a diagram of a synthetic scheme for making compounds 6 and 7 according to an embodiment of the present invention.
Figure 3:
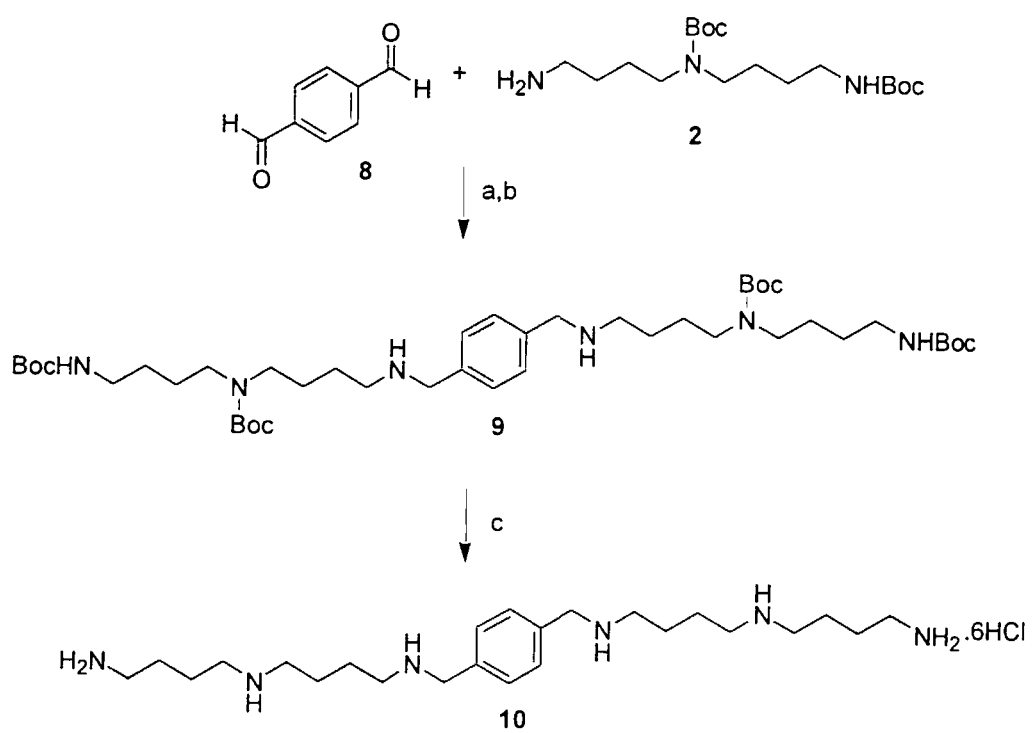
FIG. 3 depicts a synthetic scheme for making compounds 9 and 10 according to an embodiment of the present invention.
Figure 4:
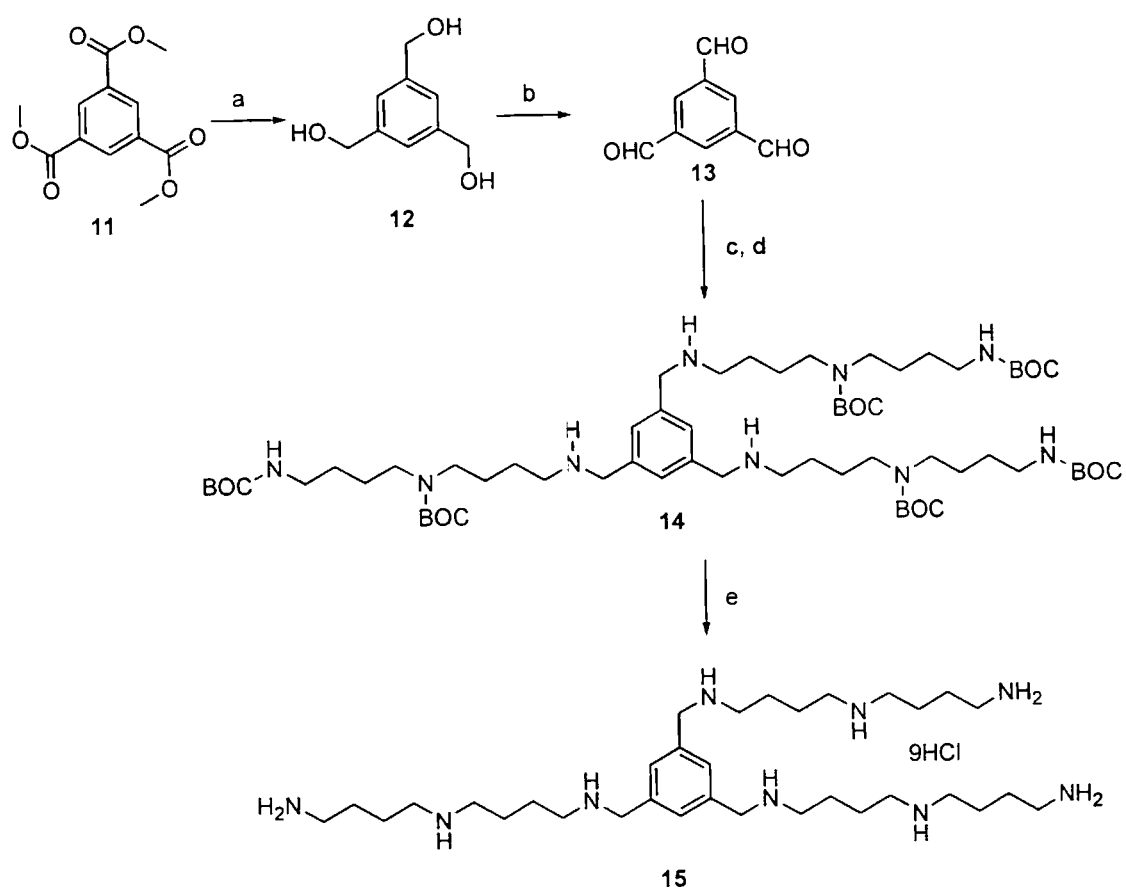
FIG. 4 presents a synthetic scheme for making compounds 14 and 15 according to an embodiment of the present invention.
Figure 5:
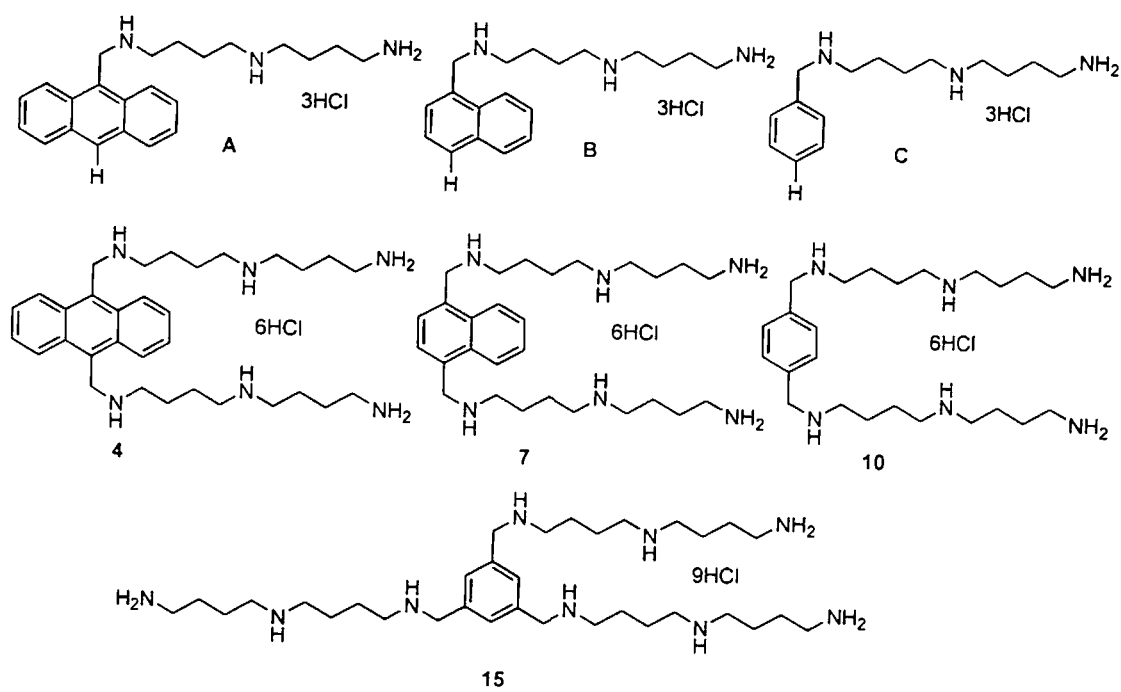
FIG. 5 depicts the formulas for the highly active, novel compounds of the present invention, compounds 4, 7, 10 and 15, compared to compounds A, B and C, which were previously described.

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below.

Any publications, patent applications, patents, or other references mentioned herein are incorporated by reference in their entirety. In case of conflict, the present specification, including any definitions, will control. For example, the invention disclosed herein is an extension of the experimental work that led to application Ser. No. 11/372,671, which was published as US 2007/0088081 on Apr. 19, 2007, and which is commonly owned with the present application and is incorporated herein by reference in its entirety. This previously described invention includes parent compounds A, B and C, over which the presently disclosed compounds represent an unexpectedly surprising and significant improvement.

In addition, in this application the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

As used herein, the term "pharmaceutically acceptable salt" is intended to describe any form (such as a salt of these amine systems with an organic carboxylic acid like acetic acid or toluene-sulfonic acid or methane sulfonic acid or an inorganic acid such as HCl, HBr, phosphoric acid, or a related group or prodrug) of a compound of the invention, which, upon administration to a subject, provides the mature or base compound and does not cause undue harmful side-effects in the subject. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art.

For example, it is a well-known practice in pharmaceutical science to use pharmaceutically acceptable acid salts of amine derivatives to facilitate their long storage and dosing as aqueous solutions. The examples listed in this invention comprise polyamine salts derived from a pharmaceutically acceptable acid (such as HCl or others) with or without the use of a pharmaceutically acceptable carrier (such as water or other). Such salts can be derived from either inorganic or organic acids, including for example hydrochloric, hydrobromic, acetic, citric, fumaric, maleic, benzenesulfonic, and ascorbic acids. The pharmaceutical compositions obtained by the combination of the carrier and the polyamine salt will generally be used in an effective dosage necessary to elicit the desired biological effect. This includes its use in an antineoplastic effective amount or in a lesser amount when used in combination with other biologically active agents.

"Polyamine" relates to a polyamine compound or a polyamine conjugate according to an embodiment of the present invention, which have a polyamine message which is recognized by the polyamine transport system on the surface of cells and have enhanced uptake into cells with highly active polyamine transporters over those which do not, (e.g., CHO vs. CHO-MG cells).

The term "transporter" is used to describe the cellular process of binding and/or importing a chemical entity which is outside the cell. The chemical entity in this case is the polyamine or polyamine conjugate, i.e. a polyamine compound or scaffold covalently attached to an agent such as a treatment drug or toxic agent.

The term "conjugate" is used to describe a polyamine compound according to the present invention which is associated with, for example, covalently bound, to a treatment agent (e.g., a cytotoxin such as an anthracenyl methyl unit) or to a known agent having anti-cancer properties, e.g., doxorubicin.

"Cell selectivity" denotes the ability of a polyamine or polyamine conjugate of the present invention to preferentially enter in enhanced levels cells with highly active polyamine transporters (e.g. CHO cells or B16 melanoma cells) over those that have lower polyamine transport activity (e.g. CHO-MG cells or MeI-A cells).

"$IC_{50}$ value" is the concentration of drug needed to kill 50% of the relative cell population. The lower the value the more cytotoxic the drug is to that cell type.

"$K_i$ value" reflects the affinity of the drug architecture for the polyamine transporter. The lower the value of the $K_i$, the higher the affinity of the drug for the polyamine transporter.

L1210 cells are mouse leukemia cells and are a standard well used benchmark for evaluating cytotoxicity of new drug systems, especially polyamine containing drugs.

Chinese hamster ovary cells (CHO cells) have an active polyamine transporter. This cell type is very susceptible to drugs which use the polyamine transporter system to gain access to cells (i.e. polyamine conjugates).

Chinese hamster ovary cells which are chemically mutated to be polyamine transport-deficient will be referred to as the CHO-MG cell line. This cell type should have lower susceptibility to polyamine conjugates which use the polyamine transporter to gain access to cells, since it does not have an active transporter to facilitate their uptake.

B16 cells are melanoma, skin cancer cells with highly active polyamine transporters. These cells should be very susceptible to polyamine conjugates which use the polyamine transporter to gain access to cells.

MeI-A cells are normal melanocytes, skin cells which have moderately active polyamine transporters. These cells should be moderately susceptible to polyamine-conjugates, but less so than the B-16 cells.

As noted above, because cancer cells rely on polyamine transport in order to sustain their growth rate, this provides an opportunity to selectively target rapidly dividing cancer cells via their heavy reliance on polyamine import. Drug-polyamine conjugates, which attach a smart polyamine message to a known cytotoxic agent, have been shown to have enhanced cytotoxicity to cancer cells (mouse melanoma, B-16 cells) over their normal cell counterparts (MeI-A) in vitro. Previous anthracene-polyamine conjugates described in U.S. Pat. No. 7,001,925 are mono-substituted analogues with good selectivity for targeting the PAT. This disclosure details the synthesis and superior PAT targeting abilities of a di-substituted series of anthracene-polyamine conjugates and other arylalkylpolyamines (di-substituted benzyl and naphthyl analogues).

The PAT targeting selectivity was determined using a Chinese hamster cell assay. The CHO wild type cells have active polyamine transport activity and therefore should be very susceptible to the polyamine conjugate and give low $IC_{50}$ values. The $IC_{50}$ value is the concentration of the drug required to kill 50% of the relative cell population. The lower the value the more cytotoxic the drug is to that cell type. In contrast, the mutant CHO-MG cells, which have no PAT activity are not as sensitive to the polyamine conjugate (which is unable to enter these cells via the defective PAT) and give higher $IC_{50}$ values. We express these as a ratio of the $IC_{50}$ value in CHOMG/$IC_{50}$ value in CHO. The higher the ratio the more PAT selective is the polyamine conjugate drug. Cytotoxic compounds, which do not use the PAT for cellular entry, would give ratios near 1.

The previous most selective compounds were the naphthyl and anthracene-homospermidine conjugates (with CHOMG/CHO $IC_{50}$ ratios near 150). These are described in application Ser. No. 11/372,671, which was published as US 2007/0088081 on Apr. 19, 2007, and which is commonly owned with the present application and is incorporated herein by reference in its entirety, as noted above. Surprisingly, it has been discovered that by repeating this message (homospermidine) on the other side of the molecule we were able to dramatically and unexpectedly improve the PAT targeting (e.g. CHOMG/CHO $IC_{50}$ ratio>2200) ability of these new compounds (4, 7, 10 and 15). The novel compounds of the present invention are synthesized via the synthetic schemes illustrated in FIGS. 1-4. In these synthetic schemes, the reagents used are as follows: a) LiAlH$_4$/THF; b) PCC/ CH$_2$Cl$_2$; c) 25% MeOH/CH$_2$Cl$_2$; 2-d) 50% MeOH/CH$_2$Cl$_2$/ NaBH$_4$; e) 4N HCl/EtOH.

Synthetic Preparation of the Novel Compounds

Compound 3

(4-tert-Butoxycarbonylamino-butyl)-(4-{[10-({4-[tert-butoxycarbonyl-(4-tert-butoxycarbonylamino-butyl)-amino]-butylamino}-methyl)-anthracen-9-ylmethyl]-amino}-butyl)-carbamic acid tert-butyl ester To a stirred solution of 2 (845 mg, 2.35 mmol) in 25% MeOH/CH$_2$Cl$_2$ (20 mL), was added a solution of Anthracene-9,10-dicarbaldehyde (250 mg, 1.07 mmol) in 25% MeOH/CH$_2$Cl$_2$ (15 mL) under N2. The mixture was stirred at room temperature overnight until the imine formation was complete (monitored by $^1$H NMR (CDCl$_3$) signal at 11.40 ppm disappeared). The solvent was removed in vacuo, the solid residue dissolved in 50% MeOH/CH$_2$Cl$_2$ (40 mL) and the solution was cooled to 0° C. NaBH$_4$ (6.42 mmol) was added in small portions to the solution and the mixture was stirred at rt overnight. The solvent was removed in vacuo, the solid residue dissolved in CH$_2$Cl$_2$ (50 mL) and washed with 10% aq. Na$_2$CO$_3$ solution (3×30 mL). The CH$_2$Cl$_2$ layer was separated, dried over anhydrous Na$_2$SO$_4$, filtered and removed in vacuo to give an oily residue. The oil was purified by flash column chromatography to yield the product 3 as a pale yellow viscous oil (92%), R$_f$=0.3 (5% MeOH/0.5% NH$_4$OH/CH$_2$Cl$_2$; $^1$H NMR (CDCl$_3$) δ 8.36 (d, 4H), 7.50 (d, 4H), 7.48 (m, 2H), 4.82 (br m, 2H), 4.68 (s, 4H), 3.13 (m, 12H), 2.87 (t, 4H), 1.65-1.30 (m, 52H); $^{13}$C NMR (CDCl$_3$) δ 155.9, 155.4, 131.9, 129.9, 125.6, 124.8, 79.1, 78.9, 53.5, 50.3, 46.9, 46.7, 46.0, 40.2, 28.6, 28.5, 27.5. HRMS (FAB) m/z calcd. for C$_{52}$H$_{84}$N$_6$O$_8$ (M+H)$^+$ 921.6423, found 921.6414.

Compound 4

N-(4-Amino-butyl)-N'-(10-{[4-(4-amino-butylamino)-butylamino]-methyl}-anthracen-9-ylmethyl)-butane-1,4-diamine, Hydrochloride salt A solution of BOC-protected 3 (890 mg, 0.97 mmole) was dissolved in absolute ethanol (13 mL) and stirred at 0° C. for 10 minutes. A 4N HCl solution (22 mL) was added to the reaction mixture dropwise and stirred at 0° C. for 20 minutes and then at room temperature overnight. The solution was concentrated in vacuo to give 4 as a yellow solid in 95% yield. $^1$H NMR (D$_2$O) δ 8.19 (d, 4H), 7.79 (d, 4H), 4.83 (s, 4H), 3.30 (t, 4H), 3.11 (m, 12H), 1.79 (m, 16H); $^{13}$C NMR (D$_2$O): δ 129.7, 127.7, 124.7, 124.0, 47.7, 47.2, 47.1, 42.8, 39.0, 24.2, 23.2, 23.1. HRMS (FAB) calcd for C$_{32}$H$_{52}$N$_6$.6HCl [(M+2H-6HCl)/2]$^+$ 261.2199. Found 261.2199.

Compound 6

(4-tert-Butoxycarbonylamino-butyl)-(4-{[4-({4-[tert-butoxycarbonyl-(4-tert-butoxylcarbonylamino-butyl)-amino]-butylamino}-methyl)-naphthalen-1-ylmethyl]-amino}-butyl)-carbamic acid tert-butyl ester To a stirred solution of 2 (468 mg, 1.30 mmol) in 25% MeOH/CH$_2$Cl$_2$ (20 mL), was added a solution of Naphthalene-1,4-dicarbaldehyde (200 mg, 1.09 mmol) in 25% MeOH/CH$_2$Cl$_2$ (15 mL) under N2. The mixture was stirred at room temperature overnight until the imine formation was complete (monitored by $^1$H NMR (CDCl$_3$) signal at 11.40 ppm disappeared). The solvent was removed in vacuo, the solid residue dissolved in 50% MeOH/CH$_2$Cl$_2$ (40 mL) and the solution was cooled to 0° C. NaBH$_4$ (6.53 mmol) was added in small portions to the solution and the mixture was stirred at rt overnight. The solvent was removed in vacuo, the solid residue dissolved in CH$_2$Cl$_2$ (50 mL) and washed with 10% aq. Na$_2$CO$_3$ solution (3×30 mL). The CH$_2$Cl$_2$ layer was separated, dried over anhydrous Na$_2$SO$_4$, filtered and removed in vacuo to give an oily residue. The oil was purified by flash column chromatography to yield the product 6 as a pale yellow viscous oil (60%), R$_f$=0.3 (7% MeOH/0.5% NH$_4$OH/CH$_2$Cl$_2$; $^1$H NMR (CDCl$_3$) δ 8.12 (m, 2H), 7.50 (m, 2H), 7.38 (s, 2H), 4.87 (br m, 2H), 4.19 (s, 4H), 3.10 (m, 12H), 2.73 (t, 4H), 1.65-1.35 (m, 52H); $^{13}$C NMR (CDCl$_3$) δ 155.9, 155.4, 135.3, 132.0, 125.7, 125.4, 124.2, 79.1, 51.7, 49.7, 46.9, 46.7, 40.2, 28.5, 28.5, 27.4, 26.7, 26.1, 25.8. HRMS (FAB) m/z calcd. for C$_{48}$H$_{82}$N$_6$O$_8$ (M+H)$^+$ 871.6267, found 871.6211.

Compound 7

N-(4-Amino-butyl)-N'-(4-{[4-(4-amino-butylamino)-butylamino]-methyl}-naphthalen-1-ylmethyl)-butane-1,4-diamine, Hydrochloride salt A solution of BOC-protected 3 (500 mg, 0.57 mmole) was dissolved in absolute ethanol (13 mL) and stirred at 0° C. for 10 minutes. A 4N HCl solution (22 mL) was added to the reaction mixture dropwise and stirred at 0° C. for 20 minutes and then at room temperature overnight. The solution was concentrated in vacuo to give 7 as a yellow solid in 94% yield. $^1$H NMR (D$_2$O) δ 8.20 (m, 2H), 7.78 (m, 2H), 7.72 (s, 2H), 4.83 (s, 4H), 3.28 (t, 4H), 3.11 (t, 8H), 3.04 (t, 4H), 1.85-1.73 (m, 16H); $^{13}$C NMR (D$_2$O): δ 131.3, 129.3, 128.6, 128.0, 123.8, 48.2, 47.3, 47.2, 47.1, 39.0, 24.2, 23.2, 23.1. HRMS (FAB) calcd for C$_{28}$H$_{o5}$N$_6$.6HCl (M+H-6HCl)$^+$ 471.4170. Found 471.4155.

Compound 9

(4-tert-Butoxycarbonylamino-butyl)-{4-[4-({4-[tert-butoxycarbonyl-(4-tert-butoxy carbonylamino-butyl)-amino]-butylamino}-methyl)-benzylamino]-butyl}-carbamic acid tert-butyl ester To a stirred solution of 2 (885 mg, 2.46 mmol) in 25% MeOH/CH$_2$Cl$_2$ (20 mL), was added a solution of Benzene-1,4-dicarbaldehyde (150 mg, 1.12 mmol) in 25% MeOH/CH$_2$Cl$_2$ (15 mL) under N2. The mixture was stirred at room temperature overnight until the imine formation was complete (monitored by $^1$H NMR (CDCl$_3$)). The solvent was removed in vacuo, the solid residue dissolved in 50% MeOH/CH$_2$Cl$_2$ (40 mL) and the solution was cooled to 0° C. NaBH$_4$ (6.71 mmol) was added in small portions to the solution and the mixture was stirred at rt overnight. The solvent was removed in vacuo, the solid residue dissolved in CH$_2$Cl$_2$ (50 mL) and washed with 10% aq. Na$_2$CO$_3$ solution (3×30 mL). The CH$_2$Cl$_2$ layer was separated, dried over anhydrous Na$_2$SO$_4$, filtered and removed in vacuo to give an oily residue. The oil was purified by flash column chromatography to yield the product 9 as a pale yellow viscous oil (54%), R$_f$=0.38 (6% MeOH/0.5% NH$_4$OH/CH$_2$Cl$_2$; $^1$H NMR (CDCl$_3$) δ 7.17 (m, 4H), 4.83 (br m, 2H), 3.68 (s, 4H), 3.06 (m, 12H), 2.55 (m, 4H), 1.60-1.21 (m, 52H); $^{13}$C NMR (CDCl$_3$) δ 155.9, 155.4, 138.8, 128.1, 126.8, 79.1, 78.8, 64.3, 53.5, 49.0, 46.9, 46.7, 40.2, 28.5, 28.5, 27.5, 27.3, 26.6, 26.0, 25.6. HRMS (FAB) m/z calcd. for $C_{44}H_{80}N_6O_8$ $(M+H)^+$ 821.6110, found 821.6083.

Compound 10

N-(4-Amino-butyl)-N'-(4-{[4-(4-amino-butylamino)-butylamino]-methyl}-benzyl)-butane-1,4-diamine, Hydrochloride salt A solution of BOC-protected 9 (495 mg, 0.60 mmole) was dissolved in absolute ethanol (13 mL) and stirred at 0° C. for 10 minutes. A 4N HCl solution (22 mL) was added to the reaction mixture dropwise and stirred at 0° C. for 20 minutes and then at room temperature overnight. The solution was concentrated in vacuo to give 4 as a yellow solid in 93% yield. $^1$H NMR ($D_2O$) δ 7.59 (m, 4H), 4.30 (s, 4H), 3.17 (t, 4H), 3.11 (t, 8H), 3.05 (t, 4H), 1.78 (m, 16H); $^{13}$C NMR ($D_2O$): δ 132.4, 130.9, 64.3, 51.1, 47.4, 47.3, 47.1, 39.3, 24.5, 23.4, 23.3. HRMS (FAB) calcd for $C_{24}H_{48}N_6$.6HCl [(M+2H-6HCl)/2]+ 211.2043. Found 211.2043.

Compound 12

1,3,5-Tris(hydroxymethyl)benzene

Trimethyl-1,3,5-benzenetricarboxylate 11 (2 g, 7.9 mmol, Acros Chemicals) in dry THF (30 mL) was added through a pressure-equalized addition funnel into a 250-mL flask containing $LiAlH_4$ (0.90 g, 23.6 mmol) in dry THF (65 mL) at 0° C. under a N2 atmosphere. The mixture was allowed to warm to room temperature and was then stirred for 4 h. The reaction was quenched by the slow addition of a 1:1 mixture of Celite and KHSO4. The suspension was filtered, and the Celite was washed with MeOH (100 mL). The solvent was removed under reduced pressure and triol 12 was obtained in 78% yield (1.05 g). $^1$H NMR of the product matched that of the authentic material: $^1$H NMR (300 MHz, DMSO) δ 7.18 (s, 3H), 4.50 (s, 6H).

Compound 13

1,3,5-Triformyl benzene 1,3,5-Tris(hydroxymethyl)benzene: (1.05 g, 6.25 mmol) was suspended in $CH_2Cl_2$ (25 mL), and solid pyridinium chlorochromate (5.98 g, 27.74 mmol) was added. After 30 min of stirring, the reaction mixture was diluted with acetone (10 mL), and was allowed to stir for 3 h. The precipitated chromium salts were filtered off and washed with $CH_2Cl_2$. The organic phase was washed with a saturated solution of aqueous $Na_2CO_3$ three times, and dried over anhydrous $Na_2SO_4$. Filtration through a silica gel column eluting with $CH_2Cl_2$ afforded 13 as white crystals (51%, 0.51 g). $^1$H NMR (300 MHz, $CDCl_3$) δ 10.21 (s, 3H, CHO), 8.66 (s, 3H, aromatic).

Compound 14

{4-[3,5-Bis-({4-[tert-butoxycarbonyl-(4-tert-butoxy-carbonylamino-butyl)-amino]-butylamino}-methyl)-benzylamino]-butyl}-(4-tert-butoxycarbonylamino-butyl)-carbamic acid tert-butyl ester 1,3,5-Triformyl benzene (0.180 g, 1.11 mmol) was dissolved in 25% $MeOH/CH_2Cl_2$ (10 mL). A solution of Boc-protected homospermidine 2 (1.44 g, 4.011 mmol) in 25% $MeOH/CH_2Cl_2$ (10 mL) was added via an addition funnel. The reaction mixture was stirred overnight under a N2 atmosphere. Loss of the starting material was monitored via $^1$H NMR spectroscopy and the disappearance of the aldehyde proton at 10.21 ppm. Upon conversion of the starting material, the solvent was extracted in vacuo and the crude material was redissolved in a solution of 50% $MeOH/CH_2Cl_2$. To this new solution was added $NaBH_4$ (0.45 g, 11.9 mmol) at 0° C. The solution was stirred overnight under a N2 atmosphere. The solvent was removed in vacuo and flash column chromatography (1% $NH_4OH$/5% $CH_3OH/CH_2Cl_2$) provided a mixture of the co-eluting Boc-protected homospermidine 2 and the desired product 14 (1.08 g). To aid in the chromatographic separation of 14 and 2, another reaction was carried out. The mixture was dissolved in THF (45 mL) and stirred for 20 min at 0° C. A solution of 2-(tert-butoxycarbonyloyimino)-2-phenylacetonitrile) (BOC-ON, 0.23 g, 0.93 mmol) was added dropwise with constant stirring. After the addition was complete, the reaction was stirred for 2 h at 0° C. under a N2 atmosphere. Upon completion, the solution was concentrated in vacuo, the residue was redissolved in $CH_2Cl_2$, and washed with a saturated aqueous $Na_2CO_3$. The organic layer was separated, dried over anhydrous $Na_2SO_4$ filtered and concentrated. Flash column chromatography of the residue gave pure 14 as colorless oil (79 mg). Yield: 6%. $R_f$=0.35 (1% $NH_4OH$/6.5% $CH_3OH/CH_2Cl_2$); $^1$H NMR (300 MHz, $CDCl_3$) δ 7.14 (s, 3H, aromatic), 4.69 (s, 3H, NH), 3.75 (s, 6H, $CH_2$), 3.15 (m, 18H, $CH_2$), 2.65 (t, 6H, $CH_2$), 1.65-1.15 (m, 78H, $CH_2$, $CH_3$); $^{13}$C NMR ($CDCl_3$): δ 156.0, 155.6, 140.5, 126.7, 79.3, 79.2, 54.1, 49.5, 47.1, 46.9, 40.4, 28.7, 28.6, 27.6, 27.5, 26.8, 26.1, 25.8. HRMS (FAB) m/z calcd for C63H117O12N9 $(M+H)^+$ 1192.8894, found 1192.9008.

Compound 15

N-(4-Amino-butyl)-N-(3,5-bis-{[4-(4-amino-butylamino)-butylamino]-methyl}-benzyl)-butane-1,4-diamine, nona-Hydrochloride Salt Compound 14 (79 mg, 0.066 mmol) was dissolved in absolute ethanol (8 mL) and stirred at 0° C. for 10 minutes. 4N HCl solution (10 mL) was added dropwise to the reaction mixture and stirred at 0° C. for 20 minutes and then at room temperature overnight. The solution was concentrated in vacuo to give 15 as a white solid in 97% yield (59 mg). $^1$H NMR (300 MHz, $D_2O$) δ 7.64 (s, 3H, aromatic), 4.32 (s, 6H, CH2), 3.18 (t, 6H, $CH_2$), 3.07 (m, 18H, $CH_2$), 1.77 (m, 24H, $CH_2$); $^{13}$C NMR ($D_2O$): δ 135.6, 135.1, 53.2, 49.8, 49.7, 41.7, 26.9, 25.8, 25.7; HRMS (FAB) m/z calcd for $C_{33}H_{78}N9Cl_9$ (M+H-9HCl)+ 592.5749, found 592.5749.

TABLE 1

Elemental analyses for compounds

| Cmpd No. | Molecular Formula | C Calcd. | C Found | H Calcd. | H Found | N Calcd. | N Found |
|---|---|---|---|---|---|---|---|
| 3 | $C_{52}H_{84}N_6O_8 \cdot 0.4H_2O$ | 67.27 | 67.23 | 9.21 | 9.07 | 9.05 | 8.87 |
| 4 | $C_{32}H_{58}N_6Cl_6 \cdot 1.3H_2O$ | 50.38 | 50.36 | 8.01 | 8.05 | 11.02 | 10.84 |
| 6 | $C_{48}H_{82}N_6O_8$ | 66.18 | 65.99 | 9.49 | 9.47 | 9.65 | 9.57 |
| 7 | $C_{28}H_{56}N_6Cl_6 \cdot 2.5H_2O$ | 45.79 | 45.94 | 8.37 | 8.25 | 11.44 | 11.37 |
| 9 | $C_{44}H_{80}N_6O_8 \cdot 0.2H_2O$ | 64.07 | 64.03 | 9.83 | 9.84 | 10.19 | 9.94 |
| 10 | $C_{24}H_{54}N_6Cl_6$ | 45.08 | 44.85 | 8.51 | 8.43 | 13.14 | 12.86 |
| 14 | $C_{63}H_{117}O_{12}N_9 \cdot 0.5H_2O$ | 62.97 | 9.90 | 10.49 | 62.85 | 9.90 | 10.39 |
| 15 | $C_{33}H_{78}N_9Cl_9 \cdot 1.5H_2O$ | 41.85 | 8.62 | 13.31 | 41.90 | 8.53 | 13.18 |

TABLE 2

CHO studies

| Cmpd | CHOMG $IC_{50}$ (μM) | CHO $IC_{50}$ (μM) | CHOMG/CHO $IC_{50}$ Ratio |
|---|---|---|---|
| A | 66.7 (±4.1) | 0.45 ± 0.10 | 148 |
| B | >100 | 0.6 ± 0.2 | >164 |
| C | >1000 | >1000 | NA |
| 4 | >100 | 0.045 ± 0.003 | >2222 |
| 7 | >100 | 0.12 ± 0.03 | >833 |
| 10 | 50.2 ± 3.8 | 0.074 ± 0.010 | 677 |
| 15 | >500 | >500 | NA |

TABLE 3

L1210 studies

| | $K_i$ (μM) | L1210 $IC_{50}$ (μM) | L1210 + DFMO $IC_{50}$ (μM) |
|---|---|---|---|
| A | 1.8 ± 0.1 | 0.30 ± 0.04 | 0.09 ± 0.01 |
| B | 3.8 ± 0.5 | 0.50 ± 0.03 | 0.43 ± 0.02 |
| C | 4.5 ± 0.8 | 36.3 ± 8.4 | ND |
| 4 | 0.39 ± 0.05 | 0.78 ± 0.07 | 0.22 ± 0.08 |
| 7 | 0.17 ± 0.02 | 0.25 ± 0.08 | ND |
| 10 | 0.52 ± 0.11 | 0.16 ± 0.01 | 0.36 ± 0.03 |
| 15 | 0.49 ± 0.02 | 122.3 ± 8.1 | 49.3 ± 10.0 |

Biological Evaluation of the Compounds

The biological evaluation of these compounds is shown in Table 2. As indicated therein, compound 4 was found superior in terms of targeting CHO cells with active polyamine transport showing a surprising $IC_{50}$ ratio of >2200! This is an order of magnitude higher than found with our previously reported compounds A and B. In our earlier report, compound C was shown to be somewhat unstable to cellular oxidases and partially degraded into homospermidine. As such, we were unable to measure its cytotoxicity and C had an $IC_{50}$ value >1000 μM in both CHO and CHOMG cell lines.

Cytotoxicity experiments were also performed in murine leukemia cells (L1210, Table 3) with and without the presence of difluoromethylornithine (DFMO), a known inhibitor of ornithine decarboxylase (the enzyme responsible for polyamine biosynthesis). Typically, when one blocks the ability of cells to synthesize polyamines, the cells respond by increasing their import of extracellular polyamines via PAT. Therefore, if our drugs are PAT-selective we should see a lowering of their respective $IC_{50}$ values in the presence of DFMO, a molecule which facilitates the drug's import. Indeed, as shown in Table 3, the $IC_{50}$'s are lower in the presence of DFMO, except for 10.

$K_i$ values indicate the binding affinity of the compounds for the PAT. Using competition experiments with radiolabeled spermidine, we were able to rank the binding affinity of the compounds for the PAT. Low $K_i$ values mean the compound has a high binding affinity for the PAT. As shown in Table 3, the di-substituted analogues 4, 7, and 10 all had significantly lower $K_i$ values (vs. A-C, respectively) and were better PAT binding agents.

Compound 4 as a Topoisomerase II (Topo-II) Catalytic Inhibitor:

Topoisomerase IIalpha (Topo IIa) is known to be highly expressed in rapidly multiplying cells such as cancers. In sheath tumors of the peripheral nerves, a difficult to treat cancer, high expressed levels of Topo IIa are associated with poor prognosis and survival.

Previously, we have tested several branched polyamine-anthracene and acridine conjugates for their ability to inhibit Topo IIa and the results were shown to be positive for all tested conjugates (see Phanstiel et al., J. Org. Chem., 2000, 65, 5590-5599; which is incorporated herein by reference in its entirety). Thus the linear polyamine-anthracene conjugates herein disclosed (e.g., compound 4) were evaluated as Topo II inhibitors. A well established in vitro Topo II assay (as used previously) allowed us to determine whether these new conjugates (previously described compound A and novel compound 4 of the present invention) have the ability to inhibit Topo II by preventing Topo IIa from decatenating (i.e., disentangling) kinetoplast DNA (kDNA). It was concluded that conjugates A and 4 were catalytic Topo-II inhibitors, where inhibition correlated positively with an increase in drug concentration. Compound 4 was superior to the previously described parent compound A, where good inhibition was observed at a concentration of 5 μM with compound 4 (i.e., significant kDNA remained undecatenated in the top well of FIG. 6, indicating Topo II inhibition). In contrast, significantly less inhibition was observed at the same concentration (5 μM) with compound A. Both conjugates were compared to a known inhibitor, Berenil (labeled 'B' in the last lane of each gel in FIG. 6), as a control.

Figure 6:
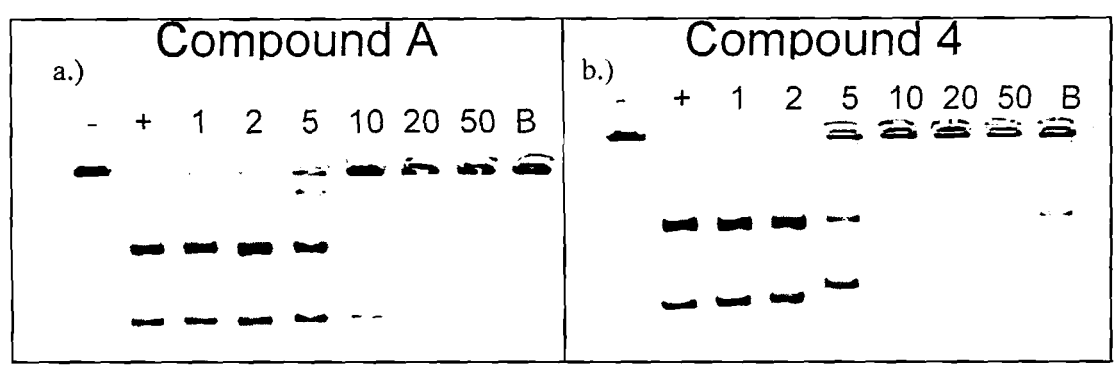
FIG. 6 shows results of several agarose gel electrophoresis analyses visualized under UV light; these are further discussed below.

In this regard, FIG. 6 shows inhibition of topoisomerase II. A negative image of agarose gel electrophoresis is visualized under UV light. Drugs were incubated with kDNA (200 ng) and Topo IIa (4 units) in reaction buffer prior to loading onto the gel. Neg. Control (−): kDNA only; Pos. Control (+): kDNA+Topo II (without conjugate); Inhibitory Control (B, rightmost lane): Berenil (50 μM). All other lanes contain the corresponding conjugate at the listed μM concentrations. Positive Topo II activity is shown by the formation of nicked open circular (NOC) DNA (middle band) and covalently closed circular (CCC) DNA (bottom band). Inhibition is shown by the negative activity of Topo II where kDNA (top band) is not decatenated and remains in the well.

When kDNA was not incubated with drug and Topo II (negative control), no migration occurred on the gel and the kDNA remained in the well as expected, which was indicated by the single top band visualized in the well. When kDNA was incubated with Topo II in the absence of drug, the top band in the well disappeared completely while two bands representing the two decatenated products could be seen. This showed that the enzyme had good activity and only inhibition rather than enzyme inactivity produced the band in the top well upon added drug. Berenil, a known inhibitor at 50 µM showed good inhibition as expected and gave most of the kDNA remaining in the well.

Accordingly, compound 4 appears to be a novel inhibitor of Topo II and, as such, is a potential agent for use against cancers where increased levels of the enzyme play a significant role in the pathogenesis of the disease.

In addition, novel compounds 4, 7, 10 and 15 represent the next generation of smart drugs and a major advance in terms of PAT-selective agents. These compounds have similar cytotoxicities to the original series A-C in L1210 cells, but are significantly more efficient in entering cells with active polyamine transporters (e.g. CHO cells). This is represented by their 10-fold increase in potency in the CHO wild type cell line over their A-C counterparts. Additionally, compounds 4 and A may also be used as Topo II catalytic inhibitors in vitro as they showed good inhibition in a well-established assay.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. An aromatic hydrocarbon di-substituted with a polyamine, said di-substituted aromatic hydrocarbon having the formula of compound 4:

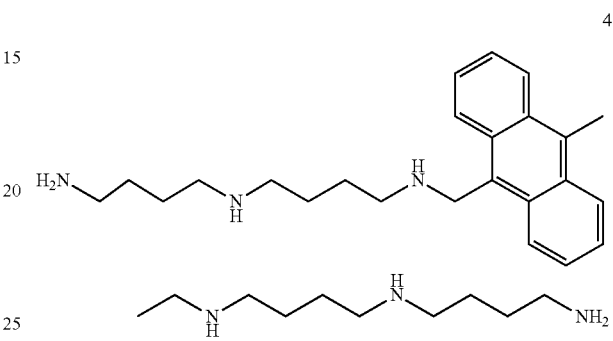

or a pharmaceutically acceptable salt thereof.

2. Compound 4, wherein compound 4 is synthesized according to the steps comprising:

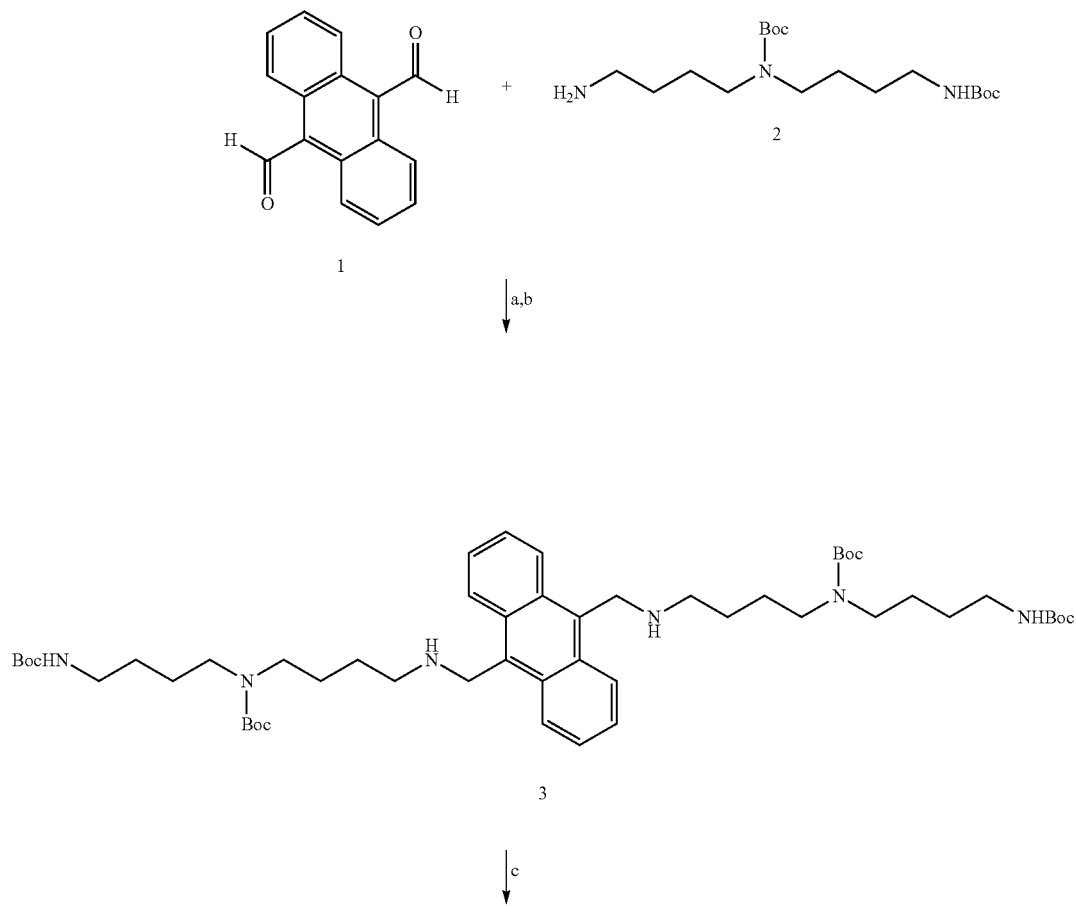

-continued

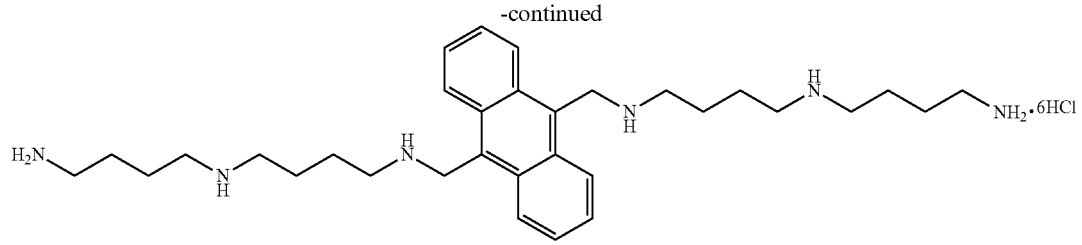

4 reacting compound 1 with compound 2 to provide compound 3, and removing the protecting groups of compound 3 to provide compound 4, wherein a is LiAlH$_4$/THF; b is PCC/CH$_2$Cl$_2$; and c is 25% MeOH/CH$_2$Cl$_2$.

3. A pharmaceutical composition comprising:
a compound comprising the formula of compound 4:

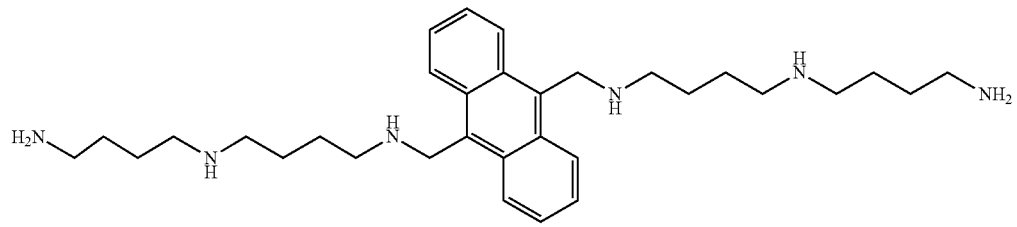

4 or a pharmaceutically acceptable salt thereof; and
a pharmaceutically acceptable carrier.

* * * * *